United States Patent
Carrero Gomez

(10) Patent No.: US 11,918,471 B2
(45) Date of Patent: Mar. 5, 2024

(54) DEVICE FOR CHECKING THE FUNCTION OF AN AORTIC VALVE

(71) Applicants: Francisco Javier Carrero Gomez, Bad Oeynhausen (DE); Michael Bogatzki, Minden (DE); Spandau Ventures GmbH, Berlin (DE)

(72) Inventor: Francisco Javier Carrero Gomez, Bad Oeynhausen (DE)

(73) Assignees: Francisco Carrero Gomez, Bad Oeynhausen (DE); Michael Bogatzki, Minden (DE); SPANDAU VENTURES GMBH, Berlin (DE)

( * ) Notice: Subject to any disclaimer, the term of this patent is extended or adjusted under 35 U.S.C. 154(b) by 198 days.

(21) Appl. No.: 16/967,907

(22) PCT Filed: Feb. 5, 2019

(86) PCT No.: PCT/DE2019/100120
§ 371 (c)(1),
(2) Date: Aug. 6, 2020

(87) PCT Pub. No.: WO2019/154461
PCT Pub. Date: Aug. 15, 2019

(65) Prior Publication Data
US 2021/0052388 A1  Feb. 25, 2021

(30) Foreign Application Priority Data
Feb. 9, 2018  (DE) .................... 10 2018 102 940.3

(51) Int. Cl.
G01L 19/00 (2006.01)
A61F 2/24 (2006.01)
(Continued)

(52) U.S. Cl.
CPC ........ A61F 2/2472 (2013.01); G01L 19/0007 (2013.01); G01L 19/08 (2013.01);
(Continued)

(58) Field of Classification Search
CPC ............ A61F 2/2472; A61F 2230/0069; A61F 2250/0069; G01L 19/0007; G01L 19/08;
(Continued)

(56) References Cited

U.S. PATENT DOCUMENTS 6,491,624 B1 * 12/2002 Lotfi ..................... A61F 2/2472
623/921
2007/0254273 A1 * 11/2007 LaFrance .............. A61F 2/2472
434/272
(Continued)

FOREIGN PATENT DOCUMENTS

WO   WO 2014/000105   1/2014

*Primary Examiner* — Jacqueline Woznicki
(74) *Attorney, Agent, or Firm* — LADAS & PARRY LLP

(57) ABSTRACT

The invention relates to a device for testing the functioning of an aortic valve by placing the device on the free end of a cylindrical tubular prosthesis inserted into the aorta, said tubular prosthesis being connected, with its other end, to the aortic wall in the region of the aortic valve. According to the invention, the device consists of a multi-part housing provided with at least one through-flow channel for a control liquid, the housing being provided, on its lower side facing the free end of the tubular prosthesis, with a peripheral sealing device that can be placed around the edge of the tubular prosthesis, and at least one pressure-measuring sensor and at least one optical sensor element for video recording being arranged on the lower side.

13 Claims, 3 Drawing Sheets

(51) Int. Cl.
*G01L 19/08* (2006.01)
*G01L 19/14* (2006.01)

(52) U.S. Cl.
CPC .... *G01L 19/142* (2013.01); *A61F 2230/0069* (2013.01); *A61F 2250/0069* (2013.01); *G01L 2019/0053* (2013.01)

(58) Field of Classification Search
CPC ..... G01L 19/142; G01L 19/0053; A61B 5/02; A61B 2576/023; Y10S 623/913
See application file for complete search history.

(56) References Cited

U.S. PATENT DOCUMENTS

| | | | | |
|---|---|---|---|---|
| 2010/0225478 | A1* | 9/2010 | McCloskey | A61B 90/06 73/37 |
| 2011/0071351 | A1* | 3/2011 | Sperling | A61F 2/2472 600/101 |
| 2015/0335290 | A1* | 11/2015 | Hunter | A61B 5/01 623/1.13 |
| 2015/0359633 | A1 | 12/2015 | Dingmann | |
| 2017/0209099 | A1* | 7/2017 | Caron | A61B 5/02158 |

* cited by examiner

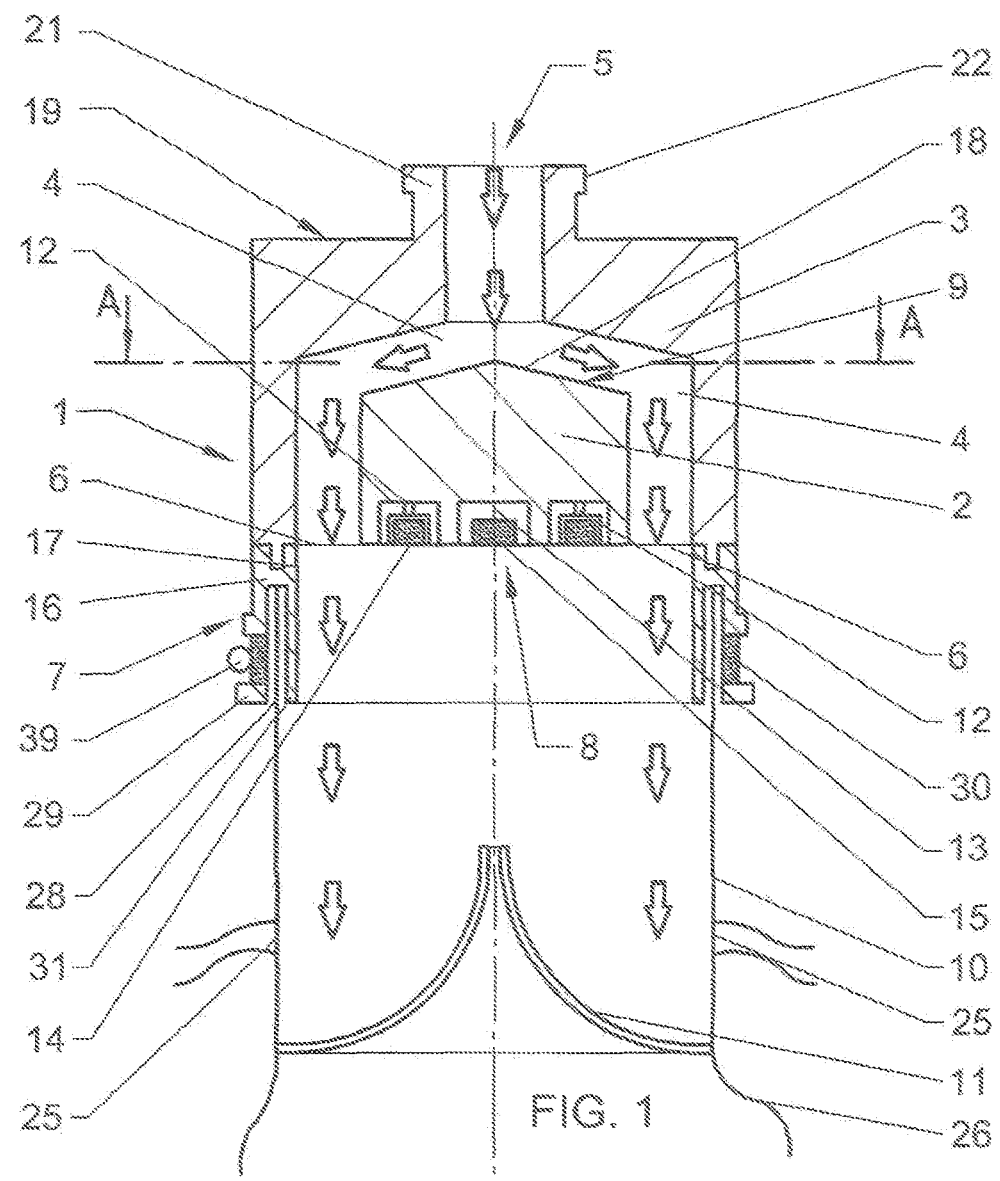
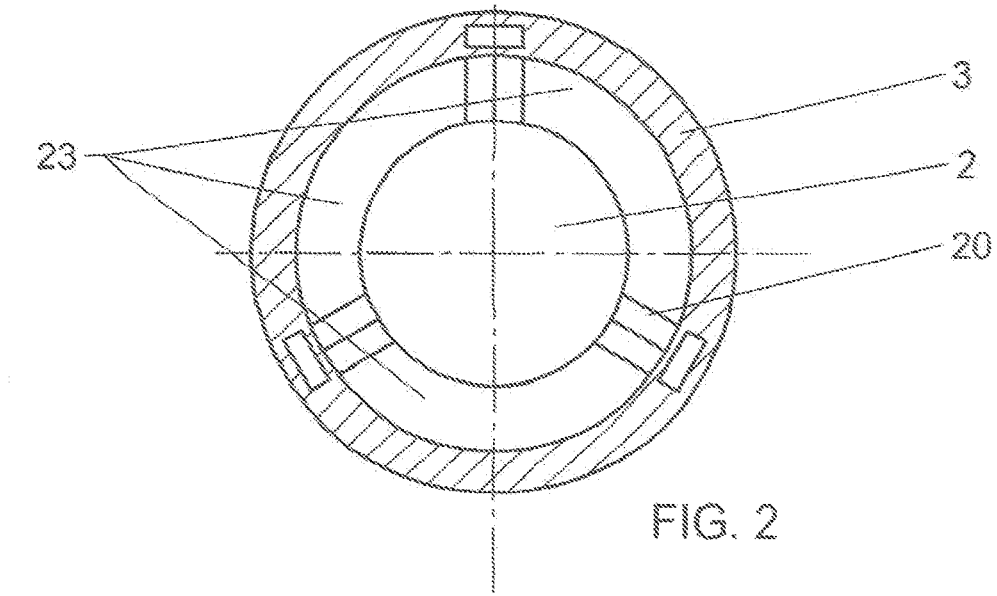

DEVICE FOR CHECKING THE FUNCTION OF AN AORTIC VALVE

TECHNICAL FIELD

The invention relates to a device for checking the function of an aortic valve by mounting the device on the free end of a cylindrical tubular prosthesis inserted into the aorta, the other end of which is connected to the aortic wall in the region of the aortic valve.

PRIOR ART

To the knowledge of the applicant, a device of the above-described type has been unknown to date in the prior art in the field of medicine.

Until now in surgeries in the region of aortic valves with an impaired function, it has been routine to suture the inserted tubular prostheses, having a corresponding diameter adapted to the patient's vein diameter, to the vein wall and to create the corresponding connection to the cardiovascular system.

Once all sutures have been completed during surgery, the created connections between the tubular prosthesis and body tissue is inspected visually for tightness.

Since surgeries in the aortic valve region are complicated, they normally require a considerable time of up to three hours. If it is revealed during the final time window of the surgery that revisions are necessary with respect to the sutures, this requires an additional expenditure of time. Viewed statistically, the risk of complications to the patient increases proportionally starting at a certain length of time, so that the normal percentage of complications increases from about 1% in such surgeries to generally 3 to 4% when additional revisions are necessary.

OBJECT OF THE INVENTION

Since it is the goal of all medical developments in surgery to decrease the percentage of complications to which a patient is exposed during a surgery and that may lead to the death of the patient, it is the object of the present invention to create a device of the above-described type with which the functioning of the aortic valve and the made connection of the utilized tubular prosthesis can be easily checked directly in order to reduce the overall necessary time in surgery and reduce the patient's risk with respect to potential complications.

OBJECT OF THE INVENTION

The posed object is solved for a device for checking the function of an aortic valve with the above-described generic features by the combination of features presented in the characterizing portion of claim 1.

It is essential to the invention that the device consists of a multipart housing provided with at least one flow channel for inspection fluid, wherein the housing is provided on its underside of the tubular prosthesis facing the free end with a peripheral sealing device that can be mounted on the edge of the tubular prosthesis, and wherein at least one pressure measuring sensor and at least one optical sensor element are provided on the underside of the housing for recording video.

The listed combination of features of the device according to the invention makes it possible to mount it on the free end of the tubular prosthesis lying opposite the aortic valve directly after connecting the tubular prosthesis to the body's own aortic wall material of the patient and, by means of the sealing device, to connect it in an air-tight and liquid-tight manner to the edge region of the tubular prosthesis.

Then inspection fluid is applied through the flow channel in the housing to the area of the tubular prosthesis below the device according to the invention and above the aortic valve, wherein a corresponding overpressure in the region of the aortic valve may be built up by the inspection fluid. The built-up pressure can be easily monitored by the pressure measuring sensor on the device.

The additional optical sensor element serves to record the region above the aortic valve and thus enables a visual check of the functioning of the aortic valve to be carried out.

At the same time due to the pressure buildup in the region in front of the aortic valve, connections made there to the cardiovascular system can be checked for tightness.

The provided use of the device according to the invention enables for the first time a check of the performed surgical measure that can provide immediate information on the quality of the result of surgery. By using the device according to the invention, the risk of expending additional time in such surgeries decreases significantly so that the overall risk of complications to the patient is reduced.

Special embodiments of the object of the invention result in combination with the technical teaching as described in claim 1 additionally from the dependent claims that refer to the main claim.

With regard to the structure of the device, it has proven to be advantageous when the flow channel has an inlet opening arranged in the top side facing away from the free end of the tubular prosthesis, and branches within the housing to a flow channel that terminates in an annular outlet opening in the underside of the housing within the peripheral sealing device. On the one hand, this measure yields easy accessibility of the flow channel in order to be fed the inspection fluid and, on the other hand, even and quick filling of the region of the tubular prosthesis between the underside of the housing and the aortic valve.

It can moreover be useful to design the structure of the housing so that the inside of the flow channel is formed by a central inner molded part as a component of the housing in which the pressure measuring sensor and the optical sensor element are accommodated, wherein the measuring surface and seating opening in the underside are exposed. This inner molded part forms a central element of the overall device and of course contains the wiring for the electronic elements.

According to a useful development, the outside of the flow channel is formed by a bell-shaped outer molded part that surrounds the central inner molded part at a distance and in which the inlet opening of the ring channel is arranged. This outer molded part can if desired be separate from the inner molded part and designed with a different diameter dimension.

By means of this measure, an adaptation to different diameters of the tubular prosthesis can be accomplished, wherein the different diameters are adapted to the cross-section of the aorta in which the tubular prosthesis is inserted. Given its many versions, the outer molded part is preferably made of plastic.

With regard to the structure of the device according to the invention, it has moreover proven to be advantageous to removably affix the sealing device on the outer molded part by means of a fixing device. This design configuration makes it possible if applicable to attach different versions of the sealing device to the outer molded part as required and thereby increase the versatility of the device according to the invention.

One version of the sealing device provides that it has an annular housing body which has a rectangular cross-section, and in which a recess is arranged for accommodating a projection of the outer molded part in one of the opposing narrow sides of the cross-section, and in which a U-shaped recess is located in the opposing narrow side for accommodating the annular upper end of the tubular prosthesis. The design with U-shaped recesses increases the strength of each connection between the outer molded part, sealing device and tubular prosthesis, and simultaneously serves to improve the sealing effect between the relevant components.

The sealing effect between the tubular prosthesis and sealing device can be additionally improved in that the outer leg of the U-shaped recess has at least one elastic sealing membrane which is pretensioned in the direction of the opposing leg of the U-shaped recess.

The pretension of the sealing membrane ensures that the upper edge of the tubular prosthesis is clamped within the U-shaped recess of the sealing device and therefore prevents drainage from the interior of the tubular prosthesis when the device according to the invention is mounted, and prevents elevated pressure of the utilized inspection fluid.

Another design configuration of the sealing device provides that the elastic sealing membrane in the region of the U-shaped recess facing the tubular prosthesis is designed double-walled, and a gap is between the parallel spaced walls of the sealing membrane in which a plurality of spring rods are arranged distributed over the perimeter of the peripheral gap which cause the pretension of the sealing membrane.

By means of this design configuration, a separation of the tasks to be carried out by the sealing membrane can be effectuated. The material of the sealing membrane in this embodiment can be optimally geared toward the sealing effect that it is to achieve with respect to the surface quality without having to take into consideration special elasticity requirements of the material. The utilized spring rods can be optimally adapted to the spring forces to be applied and therefore to the sealing forces.

In this configuration of the sealing device, it has proven to be additionally advantageous when the spring rods each have a swivel joint, wherein the swivel joints enable an angled position of the part of the sealing membrane toward the housing above the swivel joint relative to the part of the sealing membrane below the swivel joint.

Due to this design measure, the device according to the invention can be mounted very easily onto the upper end of the tubular prosthesis since the bottom end of the sealing membrane is spread outward by the swivel joint so that an enlarged overall ring gap results between the inner leg of the bottom U-shaped recess of the sealing device and the outer leg, which facilitates the insertion of the upper end of the tubular prosthesis. If the device is mounted on the end of the tubular prosthesis, the bottom part of the sealing membrane is applied to the outer side of the tubular prosthesis, again due to the swivel joint, and generates the overall pressures needed for a seal.

For special uses, it can moreover be advantageous if the inner surface of the leg of the sealing membrane facing the opposite leg of the U-shaped recess for accommodating the tubular prosthesis has a peripheral press bead projecting above the inner surface that, when the device is in a mounted state on the free end of the tubular prosthesis, engages in a corresponding recess in the inside of the opposing leg.

Because of this measure, the defined pressing surface is increased between the leg of the sealing membrane and the leg of the housing body between which the wall of the tubular prosthesis is clamped, which can increase the overall sealing effect.

For special applications, a third version of the sealing device is also conceivable. In this case, it is provided that the sealing device has an annular housing body with a rectangular cross section in which a recess is arranged in the narrow side of the cross-section directed upward for accommodating a projection of the housing (outer molded part), and in which a groove filled with a pressure-sensitive material is cut out in the outwardly directed longitudinal side of the cross-section.

This configuration makes it possible to insert the sealing device directly into the end of an aorta so that it covers the housing body of the sealing device to the outside, at least in the region of the groove filled with elastic material. Then a spring element, for example in the form of a spring ring, is placed on the outside of the aortic wall and brings the aortic wall into contact with the pressure-sensitive region of the sealing device and possibly causes a slight impression in the corresponding region. This configuration of the sealing device makes possible to be able to perform a check of aortic valves, possibly before performing a corresponding surgery, and thereby significantly expands the field of use of the device according to the invention.

DESCRIPTION OF THE FIGURES

Exemplary designs of the embodiment of the invention will be further explained below with reference to the accompanying drawings. In the figures:

FIG. 1 shows a cross-section of a first exemplary design of the device according to the invention, FIG. 2 shows a cross-section of the version of the embodiment from FIG. 1 in the region of sectional line AA.

Figure 3:
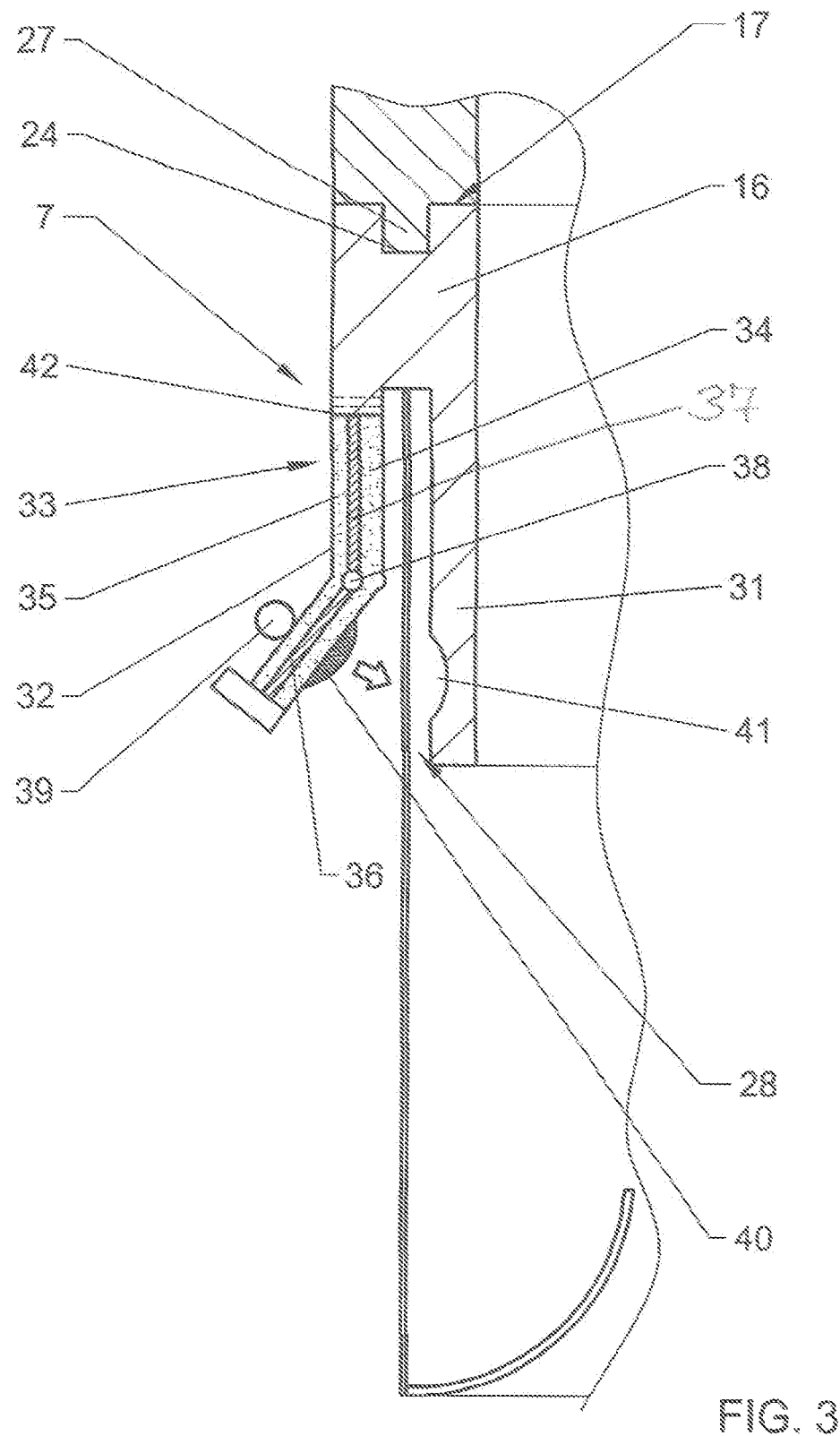
FIG. 3 shows a cross-section of the sealing device belonging to the device according to the invention in an alternative version to the one in FIG. 1.

The first design variation of the device according to the invention shown in FIG. 1 for checking the function of an aortic valve 11 possesses a housing designated overall by 1 and a sealing device designated overall by 7 as essential elements.

Corresponding to a first application, the device according to the invention is mounted on the free end of a tubular prosthesis 10 to check the function of the aortic valve 11. The tubular prosthesis 10 consists of plastic and is sutured to the end of a dissected aorta of a patient at its bottom end facing away from the upper free end. In this bottom region, there are additional vein connections 25 to the cardiovascular system of the patient that are also sutured during the overall operation to the tubular prosthesis 10. Both the vein connections 25 as well as the connection between the tubular prosthesis 10 and the aortic wall 26 must be executed absolutely liquid-tight.

The device according to the invention serves on the one hand for checking the connection of the tubular prosthesis to the body's own tissue of the patient, and on the other hand for checking the function of the aortic valve 11 arranged in the bottom region of the tubular prosthesis 10.

The housing 1 of the device according to the invention basically possesses a cylindrical exterior shape and consists of an inner molded part 2 as well as a bell-shaped outer molded part 3 surrounding the inner molded part 2. On its underside 8 facing the aortic valve 11 and the tubular prosthesis 10, the inner molded part 2 possesses a central pressure measuring sensor 13 as well as two optical sensor elements 12 adjacent thereto in the present exemplary design. The seating opening 15 of the pressure measuring sensor 13 as well as the measuring surfaces 14 of the optical sensor elements 12 are exposed to the underside 8 of the inner molded part 2.

For reasons of clarity, further details of the wiring for transmitting the measured values of the optical sensor elements 12 and the pressure measuring sensor 13 were omitted in FIG. 1. One advantageous mode of transmitting the measured values is wireless transmission for example via Bluetooth which is readily feasible today for a person skilled in the art.

On the top side facing away from the optical sensor elements 12 and the pressure measuring sensor 13, the inner molded part 2 possesses a conical diffuser surface 18 that comes to a point in the middle. The diffuser surface 18 is a component of a flow channel 4 that is formed between the outside of the inner molded part 2 and the inside of the bell-shaped outer molded part 3. The outer molded part 3 possesses an inlet opening 5 in the top side facing away from the aortic valve 11. The inlet opening 5 is provided with a connecting piece 21 and possesses a peripheral collar 22 to which a supply unit for inspection fluid, not shown in greater detail in the figure, can be connected by means of a connecting part.

The flow channel 4 branches below the inlet opening 5, wherein the diffuser surface 18 of the inner molded part 2 distributes the inspection fluid stream that is illustrated by the arrows drawn in FIG. 1 into the annular flow channel 4, one side 50 is formed by the outer molded part of the housing and the other side 49 is formed by a central inner part (2).

As can be seen from the sectional drawing in FIG. 2, the inner molded part 2 is connected to the outer molded part 3 by three bars 20 distributed evenly over the perimeter. By means of this design configuration, three ring channel sections 23 distributed over the perimeter of the flow channel result.

Toward the aortic valve 11, the flow channel 4 opens in the form of the outlet opening 6 through which the inspection fluid can flow out of the device according to the invention into the area below the inner molded part 2 that results in the interior of the tubular prosthesis 10.

The connection between the housing 1 and the top edge of the tubular prosthesis 10 is made by means of the sealing device 7.

With its special structure, the sealing device 7 serves to ensure a liquid-tight blockage of the interior of the tubular prosthesis 10 from the surroundings.

Figure 4:
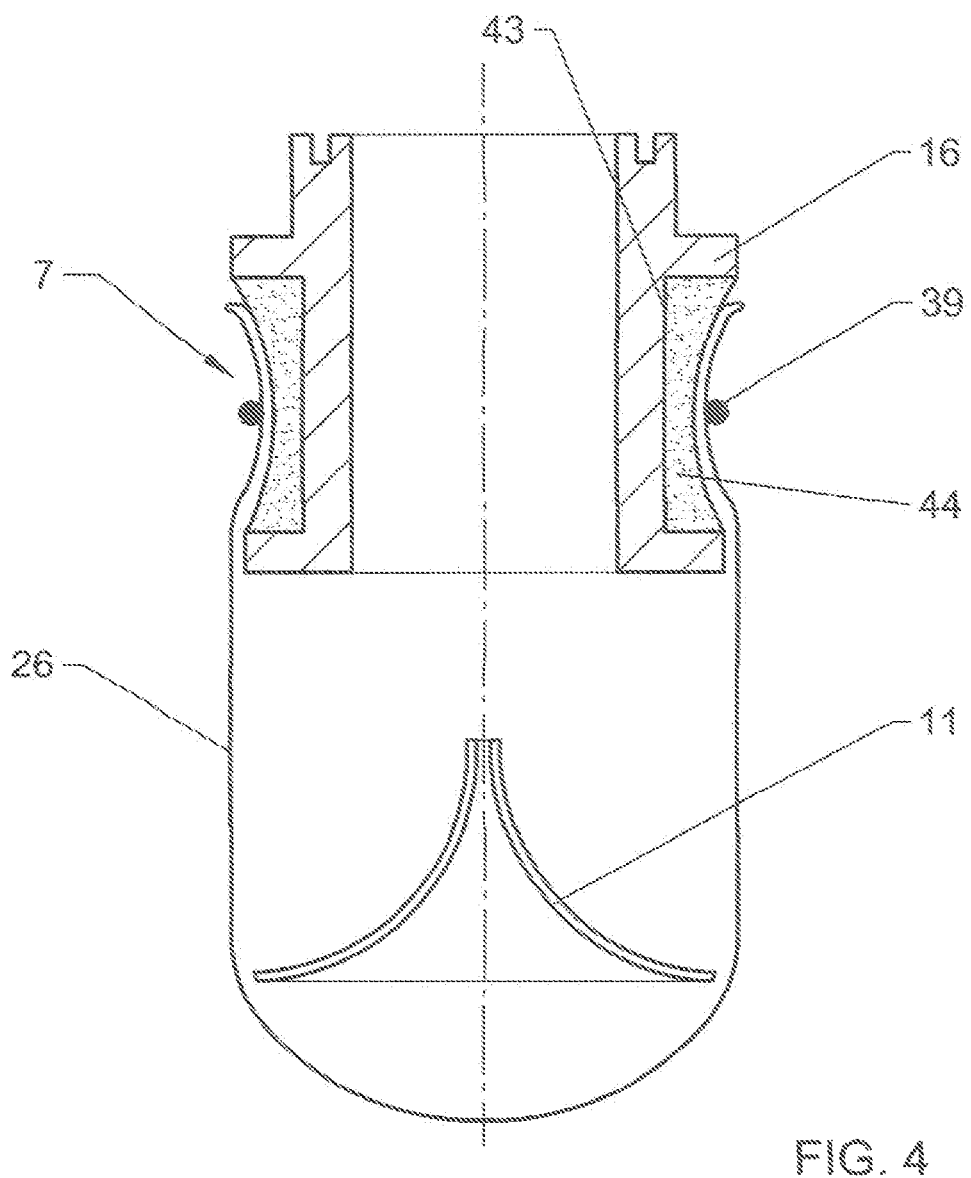
FIG. 4 shows another variation of an embodiment of the sealing device for use directly in conjunction with the end of an aortic blood vessel.

For different applications, various structural options and design configurations of the sealing device 7 are shown in FIGS. 1, 3 and 4.

The sealing device 7 as shown in FIG. 1 consists substantially of a housing body 16 in an annular configuration that substantially has a rectangular cross-section and is connected to the outer molded part 3 by means of a fixing device, for example by a latch, that is not shown in greater detail and is well-known from the prior art.

As can be seen from FIG. 1, a U-shaped recess 24 is arranged in the upper narrow side of the rectangular cross-section of the housing body 16 facing the outer molded part 3 and can be configured to be circumferential, or may only exist in individual circle segments of the housing body 16. A projection 27 on the underside of the outer molded part 3 engages in the recess 24. This design configuration reinforces the rigidity and tightness of the connection between the outer molded part 3 and housing body 16.

A U-shaped recess 28 surrounding the perimeter is also in the opposite narrow side of the housing body. The upper edge of the tubular prosthesis 10 engages in this recess 28 so that it comes to rest on the inner side against the inner side of the one leg 31 of the U-shaped recess 24 and on the opposite outer side of the other leg 29 of the U-shaped recess 28.

In order to provide corresponding tightness between the upper edge of the tubular prosthesis 10 and the sealing device 7, this outer leg 29 is produced from an elastic material, at least in a segment 30. In terms of design, this segment 30 is conceptualized such that the material is pretensioned in the direction of the parallel-spaced other leg 29 of the recess 28 so that the upper edge of the tubular prosthesis 10 is clamped between the two legs 29 and 31 once the sealing device 7 is mounted on the upper edge of the tubular prosthesis 10. The pressures in the segment 30 can be additionally supported in that a spring element in the form of a peripheral spring ring 39 is mounted on the outside of the segment 30.

In the representation in FIG. 3, another variation of the embodiment of the sealing device 7 is represented in an enlarged scale. As in the variation from FIG. 1, the sealing device 7 also consists of a peripheral housing body 16 that possesses a rectangular cross-section with one pair of sides 17, 45 being narrower than a second pair of sides 46, 47. The peripheral housing is provided with a recess 24 in its upper narrow side 17 in which a projection 27 engages as part of the outer molded part 3. Analogous to the variation in FIG. 1, a U-shaped recess with an inner leg 31 and an outer leg 32 is located in the narrow side 45 opposite the narrow side 17.

In contrast to variation 1, the sealing membrane 33 located on the outer leg 32 is configured double-walled and defines a gap 36 between its parallel-spaced walls 34 and 35. A plurality of spring rods 37 are arranged in this gap 36 that runs over the entire perimeter of the outer leg 32. When the sealing device 7 is in a mounted state, these spring rods 37 exert pressure on the outside of the tubular prosthesis 10 at the outer edge of the tubular prosthesis 10.

With respect to the configuration of the spring rods 37, the feature can be seen in FIG. 3 that these spring rods 37 have a swivel joint 38 approximately in the middle of their longitudinal extent. This swivel joint 38 enables the possibility of an angled position between the upper part of the sealing membrane 33 running substantially parallel to the outer wall of the tubular prosthesis 10 and the second region of the sealing membrane 33 lying below the swivel joint 38. This configuration establishes the possibility that the distance between the legs 31 and 32 of the U-shaped recess 28 is wider toward the opening than in the upper region. This measure makes it easier to mount the sealing device 7 on the upper free end of the tubular prosthesis 10. Once mounting has been successfully concluded, the bottom part of the sealing membrane 33 is placed against the outside of the upper edge of the tubular prosthesis 10 because of the swivel joint 38. This can occur for example with the assistance of a spring ring 39 as already depicted in the representation in FIG. 1.

The sealing effect of the sealing device 7 can be enhanced even more by arranging a projecting press bead 40 on the inside of the sealing membrane 33 that, after the bottom part of the sealing membrane 33 is placed, comes to rest against the outside of the tubular prosthesis 10 and presses it into a corresponding recess 41 in the inside of the opposite leg 31.

In order to balance the fluid pressure within the recess 28, one or more holes 42 are located in the floor region of this recess 28.

A third variation of the sealing device 7 is portrayed in FIG. 4. In this exemplary design, there is no U-shaped recess in the underside opposite the narrow side 17. Instead, there is a groove 43 in the outer wide side of the housing body 16 of the sealing device 7 that is filled with a pressure-sensitive molded body 44 consisting of elastic material.

This variation of the sealing device 7 is used when a check of an aortic valve is to be performed, and there is no tubular prosthesis 10 as is the above-described exemplary designs.

The aortic wall 26 in this exemplary design is placed over the free lower end of the housing body 16 so that it comes to rest against the molded body 44 arranged therein in the region of the groove 43. Once this is done, a spring ring 39 is placed against the outside of the aortic wall 26 as described is the other exemplary designs above that presses the aortic wall 26 against the molded body 44.

As schematically portrayed in FIG. 4, the spring ring 39 presses the aortic wall 26 into the molded body 24 due to its elastic properties so that a seal is created between the upper end of the aortic wall 26 with the device according to the invention. Finally, inspection fluid can be applied to the gap region between the aortic valve 11 and the underside of the inner molded part 2 of the housing 1 through the housing fixed to the sealing device 7 by means of the fixing device so that the function of the aortic valve 11 can be visually checked and measured by the pressure measuring sensors 12 and the optical sensor element 13.

LIST OF REFERENCE NUMBERS

1 Housing
2 Inner molded part
3 Outer molded part
4 Flow channel
5 Inlet opening
6 Outlet opening
7 Sealing device
8 Underside
9 Top side
10 Tubular prosthesis
11 Aortic valve
12 Optical sensor element
13 Pressure measuring sensor
14 Seating opening (optical sensor element)
15 Measuring surface (pressure measuring sensor)
16 Housing body
17 Narrow side
18 Diffuser surface
19 Top side
20 Bar
21 Connecting piece
22 Collar
23 Ring channel section
24 Recess
25 Vein connection
26 Aortic wall
27 Projection
28 Recess
29 Outer leg
30 Segment
31 Leg
32 Leg
33 Sealing membrane
34 Wall
35 Wall
36 Gap
37 Spring rod
38 Swivel joint
39 Spring ring
40 Press bead
41 Recess
42 Hole
43 Groove
44 Molded body

The invention claimed is:

1. A device for checking the function of an aortic valve, wherein the device is configured to be used in conjunction with a cylindrical tubular prosthesis having two ends, so that in use it may be positioned above the aortic valve, said device being configured to be mounted on a first end of a cylindrical tubular prosthesis being inserted into an aorta, wherein the second end of the prosthesis is configured to be connected to an aortic wall in a region of the aortic valve, wherein the device consists of:
  (a) a multipart housing (1) provided with an inlet opening connected to at least one flow channel (4) for a fluid which passes through the device, and
  (b) a peripheral sealing device (7) on a bottom region (8) of the housing, wherein said peripheral sealing device (7) is adapted for mounting on an edge of the first end of the tubular prosthesis (10), and
  wherein at least one pressure measuring sensor (13) and at least one optical sensor (12) are provided on the bottom region (8) of the housing for recording video to check the functioning of the aortic valve, and
  wherein the at least one flow channel (4) has an inlet opening (5) arranged in a top side (9) of the housing (I) which in use faces away from the first end of the tubular prosthesis (10), the inlet opening wherein the flow channel branches within the housing (1) to a channel that terminates in an annular outlet opening (6) at the bottom (8) of the housing.

2. The device according to claim 1, wherein one side (50) of the flow channel is formed by the a molded outer part (3) of the housing and the other side (49) of the flow channel is formed by a central inner part (2) as a component of the housing (1) in which the pressure measuring sensor (13) and the optical sensor (12) are accommodated, and a measuring surface (15) of the pressure-measuring sensor (13) and a seating opening (14) of the optical sensor (12) located at in the bottom region (8) of the housing are exposed.

3. The device according to claim 2, wherein the inner part (2) is made of metal.

4. The device according to claim 3, wherein the inner part is made of steel.

5. The device according to claim 1, wherein an outside of the at least one flow channel (4) is formed by an outer molded part (3) that surrounds a central inner molded part (2) at a distance and wherein the outer molded part contains the inlet opening (5) to the flow channel (4).

6. The device according to claim 5, wherein the sealing device (7) is removably affixed on the outer part (3).

7. The device according to claim 5, wherein the sealing device (7) has an annular housing body (16) which possesses a generally rectangular cross-section with one pair of sides (17, 45) being narrower than a second pair of sides (46, 47), one side of each pair being opposite the other side of that pair, and wherein a recess (24) is arranged for accommodating a projection (27) of the outer molded part (3) in one of the narrow sides and wherein a U-shaped recess (28) is located in the other narrow side for accommodating the first end of the tubular prosthesis (10).

8. The device according to claim 7, wherein the U-shaped recess (28) has two legs: an outer leg (29) with at least one elastic sealing membrane (33) for accommodating the tubular prosthesis (10), and a second leg (31) forming the other side of the U-shaped recess, wherein said outer leg (29) is pretensioned towards the second leg (31) of the U-shaped recess (28).

9. The device according to claim 8, wherein said pretesioning is effected by spring rods located in a peripheral gap within said outer leg urging it towards the inner leg.

10. The device according to claim 9, wherein the spring rods (37) each have a swivel joint (38) so that a part of the sealing membrane (33) located toward the housing (1) and above the swivel joint (38) may have an angled position relative to apart of the sealing membrane (33) below the swivel joint (38).

11. The device according to claim 8, wherein the outer leg (29) has a peripheral press bead (40) projecting above its inner surface such that, when the device is in a mounted state on the first end of the tubular prosthesis (10), the peripheral press bead engages in a corresponding recess (41) in the inner side of the opposing leg (31).

12. The device according to claim 5, wherein the outer molded part (3) of the housing (1) and the housing body (16) of the sealing device (7) consist of plastic.

13. The device according to claim 7, wherein the sealing mechanism (7) has a groove (43) cut out in an outwardly directed longitudinal side of the sealing mechanism and said groove is filled with a pressure-sensitive molded body (44).

\* \* \* \* \*